United States Patent [19]
Cole et al.

[11] Patent Number: 5,555,470
[45] Date of Patent: Sep. 10, 1996

[54] SINGLE WAVE LINEAR INTERFEROMETRIC FORCE TRANSDUCER

[75] Inventors: Neil M. Cole; Robert G. Dennis, both of Ann Arbor, Mich.

[73] Assignee: The Regents of the University of Michigan, Ann Arbor, Mich.

[21] Appl. No.: 386,120

[22] Filed: Feb. 9, 1995

Related U.S. Application Data

[63] Continuation of Ser. No. 134,989, Oct. 12, 1993, abandoned.

[51] Int. Cl.$^6$ ........................................ G01B 9/02
[52] U.S. Cl. ..................... 356/35.5; 356/345; 356/358
[58] Field of Search .................................. 356/345, 357, 356/358, 35.5, 244

[56] References Cited

U.S. PATENT DOCUMENTS

| | | | |
|---|---|---|---|
| 3,635,562 | 1/1972 | Catherin | 356/112 |
| 4,191,470 | 3/1980 | Butter | 356/35.5 |
| 4,263,810 | 4/1981 | Chiu | 73/800 |
| 4,565,941 | 1/1986 | Ridgeway et al. | 310/328 |
| 4,665,747 | 5/1987 | Muscatell | 356/358 |
| 4,758,091 | 7/1988 | Bodine | 356/358 |
| 4,815,213 | 3/1989 | McCabe et al. | 33/125 T |
| 4,815,855 | 3/1989 | Dixon | 356/358 |
| 4,841,778 | 6/1989 | Butler et al. | 73/800 |
| 4,930,895 | 6/1990 | Nishimura et al. | 356/356 |
| 4,938,595 | 7/1990 | Parriaux et al. | 356/356 |
| 4,938,596 | 7/1990 | Gauthier et al. | 356/360 |
| 4,948,257 | 8/1990 | Kaufman et al. | 356/354 |
| 4,979,826 | 12/1990 | Ishizuka et al. | 356/356 |
| 5,066,130 | 11/1991 | Tsukiji et al. | 356/356 |
| 5,080,466 | 1/1992 | Boothroyd et al. | 359/577 |
| 5,133,599 | 7/1992 | Sommargren | 356/349 |
| 5,164,791 | 11/1992 | Kubo et al. | 356/356 |

*Primary Examiner*—Samuel A. Turner
*Attorney, Agent, or Firm*—Harness, Dickey & Pierce, P.L.C.

[57] ABSTRACT

A Michelson interferometer is used to determine the displacement of a force loaded member, the loaded member having a reflective surface applied thereto to reflect light back to a beam splitter in the interferometer apparatus. Light is also reflected back from a reflective surface attached to a stationary member. The interaction of the reflected light from the movable and stationary member interacts to form an interference fringe pattern which may be used to determine the amount of displacement and, therefor, the force applied to the loaded member. The apparatus is comprised of a material which is substantially resistive to thermal deformation.

26 Claims, 3 Drawing Sheets

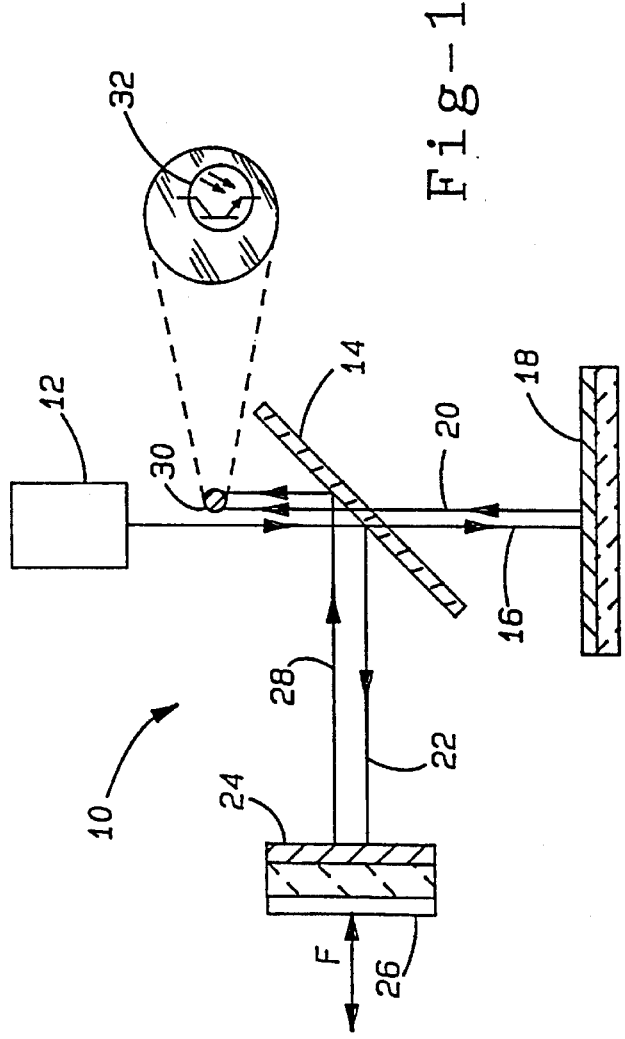
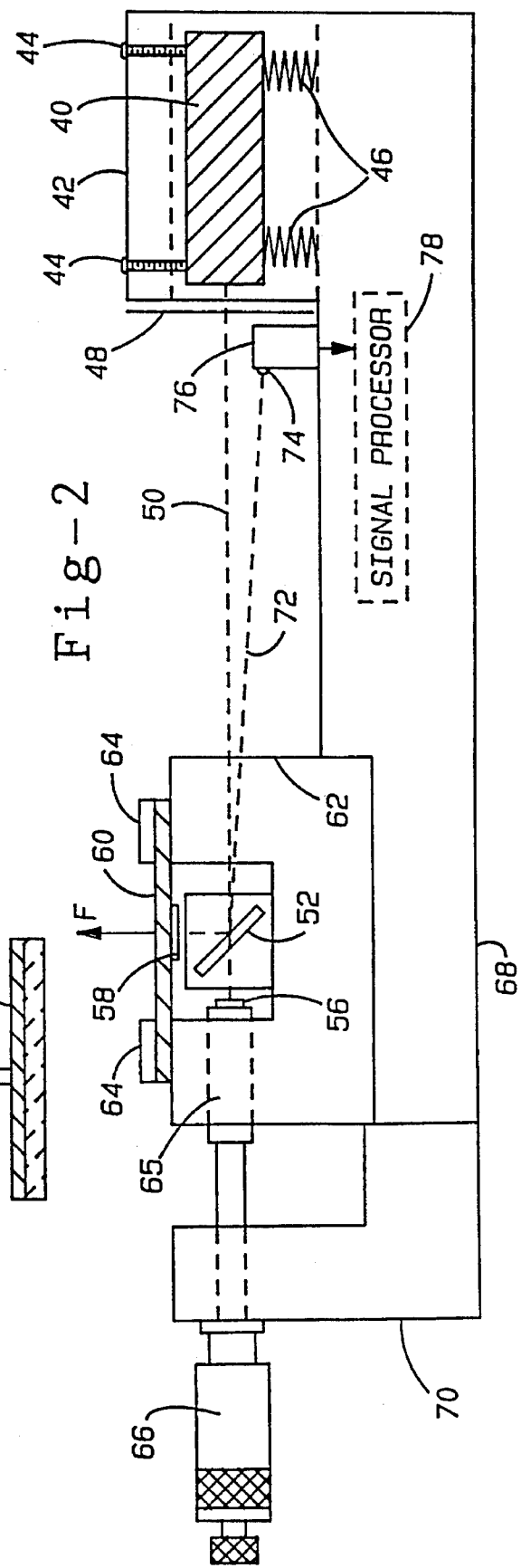

SINGLE WAVE LINEAR INTERFEROMETRIC FORCE TRANSDUCER

This is a continuation of U.S. patent application Ser. No. 08/134,989, filed Oct. 12, 1993, now abandoned.

BACKGROUND AND SUMMARY OF THE INVENTION

This invention is directed toward an extremely sensitive, high bandwidth force transducer operating on the Michelson interferometric principle and is capable of measuring minimal deflection of a load beam. More particularly, this invention has application in the study of muscle mechanics involving a single muscle fiber having high resonant frequencies and exerting minimal load forces.

In a number of experimental situations involving whole muscle and single skeleton muscle fibers, it is necessary to achieve extremely high force transduction fidelity over a large bandwidth of frequencies where measuring extremely small deflections is critical. Because force transducers typically measure displacement of a component having a known response to an applied force, the sensitivity and responsiveness of a force transducer depends upon the magnitude of deflection of the loaded element. When the applied force is very low or the force is applied to effectuate extremely small deflection in the loaded element and the bandwidth is relatively large, the inherent difficulties in measuring force are compounded.

There are a number of force transducers known in the art, but these transducers are not particularly well suited to measuring small forces or a minimal amount of displacement of the loaded member. For example, resistance strain gauges typically measure the change in resistance of a circuit resulting from deflection applied to an electrical path through the loaded member. Resistive strain gauges require large deflections and have relatively low signal-to-noise ratios. Another type of force transducer is the variable capacitance transducer which manifests a change in separation between capacitive plates through a change in the capacitance of a circuit. Capacitive transducers tend to be extremely sensitive to environmental conditions such as humidity and temperature, require sophisticated electronic equipment to detect the change in capacitance, and tend to capacitively couple to their surroundings. Yet another type of force transducer is the variable inductance based transducers which exhibits a change in applied force through a change of inductance in an electrical circuit. Inductance based transducers, however, tend to have an extremely limited frequency response. Finally, piezo-electric force transducers are less sensitive, do not respond well to low frequency inputs, and have a relatively high mechanical hysteresis. In addition to the above mentioned force transducers, several others use optical deflection or occlusion of a light path as the transducing element. Such deflection or occlusion results in a significant compromise between resonant frequency and displacement.

This apparatus is directed to a force transducer that addresses the limitations described above. In particular, the apparatus provides a force transducer having a much higher sensitivity, resonant frequency, response time, output voltage, and signal-to-noise ratio in combination than any of the above mentioned transducers. This apparatus has the added benefit that it is not capacitively or inductively coupled to the environment.

According to one embodiment of this invention, laser light is directed at a beam splitter of a Michelson interferometer. The beam splitter transmits light in the direction of a stationary reflective surface and also reflects light in the direction of a movable reflective surface. The movable reflective surface is applied to a load member to which a force is applied. When a force displaces the movable reflective surface, the reflected light from the stationary and the movable reflective surface interact to define an interference fringe pattern. The shift in one fringe of the interference fringe pattern over a substantially linear range of the fringe is measured to determine the displacement of the load member. The magnitude of the fringe displacement is in accordance with the magnitude of the force applied to the load member. The reflective surfaces of the interferometer may be applied directly to the members of the interferometer, rather than using a mirror, in order to further reduce the effects of temperature.

Further objects, features and advantages of the invention will become apparent from a consideration of the following description and the appended claims when taken in connection with the accompanying drawings.

BRIEF DESCRIPTION OF THE DRAWINGS

FIG. 1 is a drawing which demonstrates the basic principles of the Michelson interferometer as implemented in this invention;

FIG. 2 depicts one configuration of the apparatus of this invention which may be used in force transduction;

DETAILED DESCRIPTION OF THE EMBODIMENT

Figure 3:
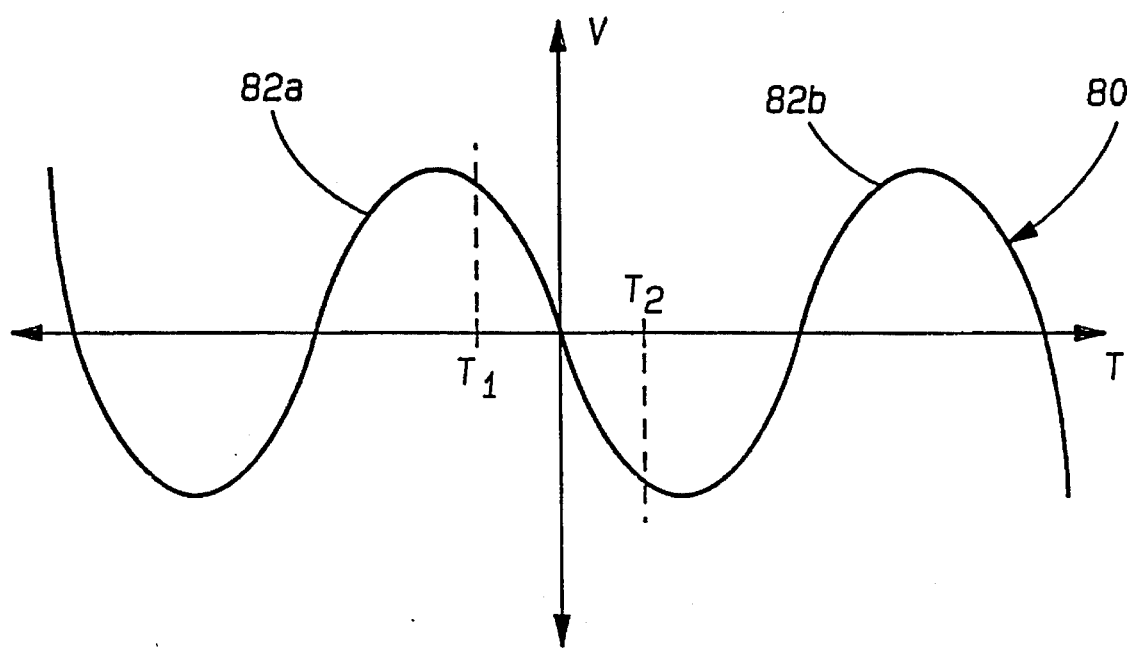
FIG. 3 depicts one example of an output waveform of the force transducer of FIG. 2.

FIG. 1 depicts generally the Michelson interferometer 10 employed in the force transducer. Light source 12 directs a monochromatic, coherent, collimated beam of light in the direction of beam splitter 14. Light incident on beam splitter 14 is separated into transmitted light 16 and is incident upon reflective surface 18 mounted on glass substrate 19 (shown as glass), which may be a mirror, a first surface reflective coating, or any other surface which reflects light of the wavelength produced by light source 12. Beam splitter 14 also reflects light 22 in the direction of movable reflective surface 24 mounted on a substrate 23 (shown as glass) which is connected to load beam 26. Reflective surface 24 yields reflected light 28 which passes through beam splitter 14 and, in cooperation with reflected light 20 and due to the coherence of light illuminated from light source 12, produces an interference fringe pattern 30. Interference fringe pattern 30 is detected by phototransistor 32 whose output signal, to be described with respect to FIG. 3, may be input to a signal processing unit in order to determine a shift in interference fringe pattern 30. Phototransistor 32 may optionally be a phototransistor photodiode, or the like.

The interference fringe pattern 30 results from constructive and destructive interference of the coherent light produced by light source 12. Beams of reflected light 20 and 28 from reflective surfaces 18 and 24, respectively, are superimposed one onto the other via beam splitter 14. If a force F is applied to load member 26, producing a displacement of movable reflective surface 24, the interference fringes shift. If the degree of shift of the interference fringes can be determined, the displacement of load member 26 may also be determined. The displacement of load member 26 is associatable with a corresponding force producing such deflection, so that the shift in the fringe pattern may be associated with the force F applied to load member 26.

FIG. 2 depicts one apparatus of this invention which may be used to implement the interferometric force transducer. Light source 40 produces a monochromatic, coherent, collimated source of light, typically in a visible wavelength (400 to 700 nm) in order to facilitate alignment and debugging, but any wavelength of light may theoretically be used. In this embodiment, a helium-neon (He—Ne) laser ($\lambda$=632.8 nm) and a diode laser ($\lambda$=670 nm) have been used. Laser diodes include many of the advantages of semi-conductor devices such as reduced power consumption, heat dissipation, reduced size, and significant cost reduction. He—Ne lasers, on the other hand, produce significantly less broadband radio frequency (RF) output noise and a greater coherence length. Light source 40 is positioned within laser housing 42 and may be directed by adjusting set screws 44 which exert a force opposing to the force exerted by set springs 46. The output light from light source 40 is attenuated by a neutral density filter 48. Attenuated light 50 strikes beam splitter 52 which produces a transmissive light beam in the direction of stationary, reflective surface 56 and a reflective light beam in the direction of movable reflective surface 58. Movable reflective surface 58 is applied to load member 60 which is connected to interferometer housing 62 via load beam clamps 64. Fixed reflective surface 56 is attached to sliding rod 65 so that fixed mirror 56 may be adjusted for calibration purposes to produce the correct path length difference. Sliding rod 65 is adjustable in accordance with the positioning of micrometer 66 which connects to system support bracket 68 via micrometer support bracket 70. Light reflected from reflective surfaces 56 and 58 produces a return light beam 72 having the same axis as attenuated light beam 50. Returned light beam 72 strikes phototransistor 74 which is mounted to phototransistor support 76. The output signal from phototransistor 74 is then input into signal processor 78 so that the shift in the interference fringe pattern may be determined.

Several important features of the apparatus described in FIG. 2 will be noted at this time. First, because it is a primary aspect of this invention to detect minimal deflection of load member 60, it is critical to minimize thermally induced dimensional changes. This may be accomplished by (1) employing the smallest geometry possible for the apparatus, (2) constructing the apparatus such that thermally induced dimensional changes occurring in response to uniform temperature changes operate to cancel each other out, and (3) constructing the interferomic portion of the device out of material (preferably a single piece) that is substantially resistant to thermally induced dimensional changes. To this end, interferometric housing 62 is constructed from INVAR-36 stainless steel as are load clamps 64 and sliding rod 65. To further minimize thermally induced dimensional changes, load beam 60 is manufactured from a low thermal expansion glass such as ZERODUR. Reflective surfaces 56, 58 may then be directly deposited onto sliding rod 65 (reflective surface 56) and load beam 60 (movable reflective surface 58). Directly depositing reflective surface 58 onto load beam 60 substantially decreases the mass of the deflecting member (load beam 60), thereby increasing the resonant frequency, and decreases the possibility of additional thermally induced dimensional changes of a mirror substrate. Alternatively, by omitting sliding rod 65 and attaching fixed reflective surface 56 directly to housing 62, it is possible to grind the entire housing 62 from solid ZERODUR.

With respect to load member 60, it is a bi-directionally sensitive element and is capable of detecting compressive as well as tensile forces. The mass of load member 60 should be limited in order to not reduce the resonant frequency and, therefore, its dynamic characteristics. Actual design of load member 60 may vary in accordance with the particular application. Load member 60 is ideally extremely rigid and may be held fixed in a number of configurations depending on the specific application. In FIG. 2, both ends of load member 60 are clamped to interferometer housing 62 via load beam clamps 64.

Figure 4A:
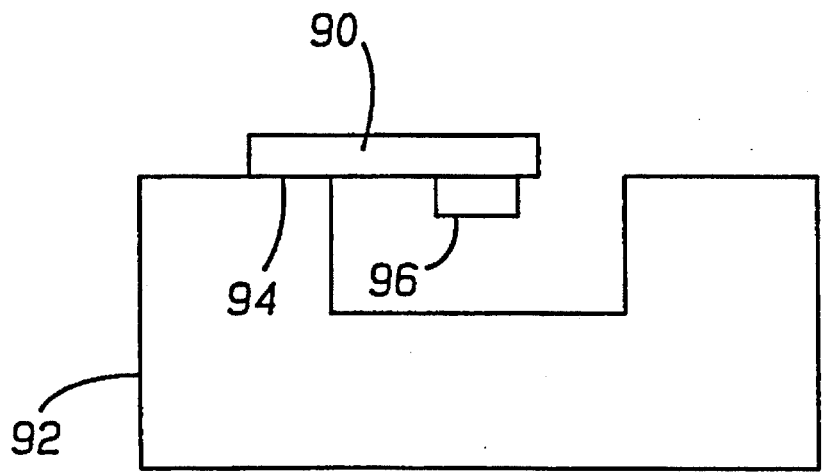
FIGS. 4a and 4b are partial views of alternative configurations for the load bearing member of the force transducer apparatus.
Figure 4B:
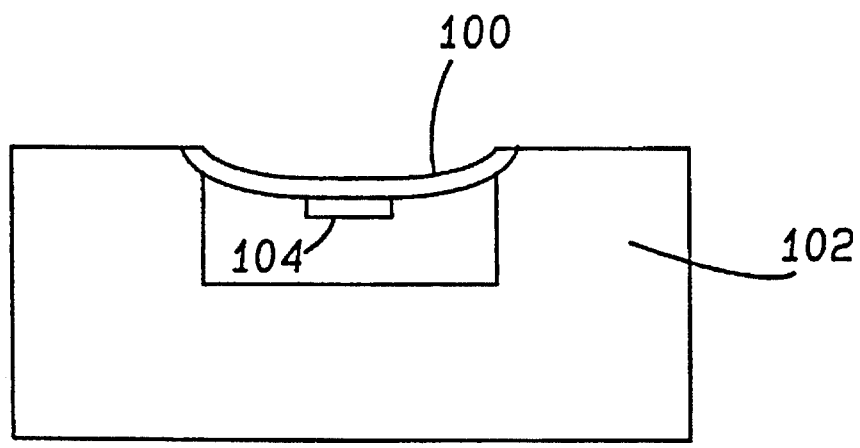

FIGS. 4a and 4b depict cantilever and diaphragm arrangements, respectively, which may be employed as a load member. Such a design yields high resonant frequency, small physical size, low mechanical hysteresis, and simplification of design. In FIG. 4a, a load beam 90 is attached to interferometer housing 92 using any of a number of known methods. Load beam 90 attaches to interferometer housing 92 at one attachment point 94, yielding a cantilever arrangement for load beam 90. A reflective surface 96 is deposited onto load beam 90 and reflects light back toward the interferometric beam splitter (not shown). The interferometer housing 92 and load beam 90 arrangement may be substituted for the housing and load beam arrangement of FIG. 2. In FIG. 4b, load beam 100 is formed in the shape of a diaphragm and attaches to interferometer housing 102. A reflective surface 104 is applied to diaphragm load beam 100 to reflect light back in the direction of a beam splitter (not shown). Either of the interferometer housing 102 and diaphragm load beam 100 arrangements may be implemented in the apparatus of FIG. 2.

FIG. 3 depicts one example of an output waveform showing an interference fringe employed in measuring the change in displacement of load beam 60 in response to a force F. In a particularly novel feature of this apparatus, it is to be noted that a change in displacement is not calculated by measuring the number of interference fringes 82a–b by which the fringe pattern has shifted. Rather, the displacement of load member 60 is determined based on a shift of a single interference fringe pattern over a nearly linear range as demonstrated by interference fringe 82a over the range $T_1$ to $T_2$. The linear portion of the output waveform is positioned so as to monitor displacement from the center of the linear portion, thereby calibrating the apparatus. While most interference fringe patterns such as those generated by a Fabry-Perot type device have substantially greater slopes between the peaks of the output waveforms than that shown in FIG. 3, measuring the shift in a single interference fringe between the peaks yields poor resolution. In the waveform of FIG. 3, because the interference fringe has a more gradual slope over a substantially linear range between $T_1$ to $T_2$, it is possible to measure the interference fringe shift (being less than 1 interference fringe) of the output waveform to determine the displacement of load member 60. Therefore, in addition to having an apparatus which is substantially resistant to dimensional changes resulting from thermal variations, the apparatus also provides an improved method for measuring the shift of the load member 60 by determining the displacement of a single interference fringe pattern.

It is to be understood that the invention is not limited to the exact construction illustrated and described above, but that various changes and modifications may be made without departing from the spirit and scope of the invention as defined in the following claims.

We claim:

1. A force transducer comprising:
   an interferometer having a beam splitter operatively connected to a housing, the housing comprising a material substantially resistive to thermal expansion;

first and second reflective surfaces for receiving light emitted from and reflecting light in the direction of the beam splitter, one of the reflective surfaces reflecting light in the direction of a light source placed opposite the beam splitter;

a load beam operatively connected to the housing, the other of the reflective surfaces being connected to the load beam and reflecting in the direction of the beam splitter, the load beam comprising a material substantially resistive to thermal expansion, the load beam deflecting in response to a force applied thereto;

photo-processing means for detecting a linear portion of an interference fringe pattern from the interferometer and generating a single output signal; and signal processing means for receiving the single output signal and determining the amount of deflection of the load beam in accordance with a shift of the linear portion of the interference fringe pattern detected by the photo-processing means, said shift measured within the linear portion of the single wave of said interference fringe pattern.

2. The apparatus as defined in claim 1 wherein the light source provides light suitable for interferometry in the direction of the beam splitter, the beam splitter transmitting light in the direction of one of the reflective surfaces and reflecting light in the direction of the other of the reflective surfaces.

3. The apparatus as defined in claim 2 wherein the light suitable for interferometry is laser light.

4. The apparatus as defined in claim 3 wherein the photo-processing means comprises one of a phototransistor, a photodiode, or an optical detector.

5. The apparatus as defined in claim 2 wherein the photo-processing means comprises one of a phototransistor, a photodiode, or an optical detector.

6. The apparatus as defined in claim 2 wherein the zero crossing of the linear portion of the interference fringe pattern is the midpoint of the range of displacement.

7. The apparatus as defined in claim 2 wherein the housing material substantially resistive to thermal expansion comprises one of INVAR-36 or ZERODUR.

8. The apparatus as defined in claim 2 wherein the load beam material substantially resistive to thermal expansion comprises one of INVAR-36 or ZERODUR.

9. The apparatus as defined in claim 1 wherein the load beam connected to the housing is attached in a cantilevered arrangement applied force for maximum sensitivity.

10. The apparatus as defined in claim 1 wherein the load beam is in the shape of a diaphragm.

11. The apparatus as defined in claim 1 wherein the load beam is receptive to an applied force between two points of interconnection to the housing to maximize response to high resonant frequencies.

12. The apparatus as defined in claim 1 wherein the signal processing means determines a direction and a magnitude of deflection of the load beam in accordance the shift of the single interference fringe pattern over the substantially linear range of the single wave of the interference fringe pattern.

13. The apparatus as defined in claim 12 further comprising calibration means to initially position the single interference fringe linear range in a suitable location for measurement.

14. A displacement sensor comprising:

an interferometer having a beam splitter operatively connected to a housing, the housing comprising a material substantially resistive to thermal expansion;

first and second reflective surfaces for receiving light emitted from and reflecting light in the direction of the beam splitter, one of the reflective surfaces reflecting light in the direction of a light source placed opposite the beam splitter;

a displaceable beam operatively connected to the housing, the other of the reflective surfaces being connected to the displaceable beam being variably deflectable and reflecting in the direction of the beam splitter, the displaceable beam comprising a material substantially resistive to thermal expansion;

photo-processing means for detecting a linear portion of an interference fringe pattern from the interferometer and generating a single output signal; and signal processing means receiving the single output signal and determining the amount of deflection of the load beam in accordance with a shift of the linear portion of the interference fringe pattern detected by the photo-processing means, the signal processing means determining the shift over the substantially linear portion, the linear portion of the fringe shifting of a single wave of the interference fringe pattern in accordance with the displacement of the displaceable beam; and means for calibrating to initially position the linear portion of the single wave of the interference fringe pattern in a suitable location for measurement.

15. The apparatus as defined in claim 14 wherein the light source provides light suitable for interferometry in the direction of the beam splitter, the beam splitter transmitting light in the direction of one of the reflective surfaces and reflecting light in the direction of the other of the reflective surfaces.

16. The apparatus as defined in claim 15 wherein the light suitable for interferometry is laser light.

17. The apparatus as defined in claim 15 wherein the photo-processing means comprises one of a phototransistor a photodiode, or an optical detector.

18. The apparatus as defined in claim 17 wherein the zero crossing of the linear portion of the interference fringe pattern represents the midpoint of the range of displacement.

19. The apparatus as defined in claim 14 wherein the photo-processing means comprises one of a phototransistor, a photodiode, or an optical detector.

20. The apparatus as defined in claim 14 wherein the housing material substantially resistive to thermal expansion comprises one of INVAR-36 or ZERODUR.

21. The apparatus as defined in claim 14 wherein the displaceable beam material is substantially resistive to thermal expansion and comprises one of INVAR-36 or ZERODUR.

22. The apparatus as defined in claim 14 wherein the displaceable beam connected to the housing is cantilevered for maximum sensitivity.

23. The apparatus of claim 14 wherein the displaceable beam is in the shape of a diaphragm.

24. The apparatus as defined in claim 14 wherein the displaceable beam is receptive to an applied force between two points of interconnection to the housing to maximize response to high resonant frequencies.

25. A method of measuring displacement, comprising the steps of:

providing an interferometer having a beam splitter operatively connected to a housing, the housing comprising a material substantially resistive to thermal expansion, the interferometer producing an interference fringe pattern;

providing first and second reflective surfaces for receiving light emitted from and reflecting light in the direction of the beam splitter, one of the reflective surfaces reflecting light in the direction of a light source placed opposite the beam splitter; p1 connecting a displaceable beam to the housing and having one of the reflective surfaces connected to the displaceable beam and reflecting in the direction of the beam splitter, the displaceable beam comprising a material substantially resistive to thermal expansion, the displaceable beam deflecting in response to a force applied thereto;

detecting a linear portion a single wave of an output interference fringe pattern produced by the interferometer and generating a single output signal; and determining the amount of deflection of the deflectable beam in accordance with a shift of the linear portion of the single wave detected by the photo-processing means, the linear portion of the fringe shifting in accordance with the displacement of the displaceable beam.

26. The method as defined in claim 25 wherein the step of determining the amount of deflection comprises measuring a direction and magnitude of the shift in the interference fringe pattern in accordance with the shift of the substantially linear portion of the single wave.

* * * * *